United States Patent [19]

Garth

[11] 4,121,911
[45] Oct. 24, 1978

[54] MANNICH BASES CONTAINING TERTIARY AMINES

[75] Inventor: Bruce Hollis Garth, Newark, Del.

[73] Assignee: E. I. Du Pont de Nemours and Company, Wilmington, Del.

[21] Appl. No.: 803,943

[22] Filed: Jun. 6, 1977

Related U.S. Application Data

[62] Division of Ser. No. 612,726, Sep. 12, 1975, Pat. No. 4,054,422.

[51] Int. Cl.$^2$ .................. C10L 1/22; C07D 295/12
[52] U.S. Cl. ............................................. 44/73; 544/402
[58] Field of Search ....................... 260/268 R; 44/73

[56] References Cited

U.S. PATENT DOCUMENTS 2,962,442  11/1960  Andress ............................. 252/51.5
4,054,422  10/1977  Garth ............................. 252/51.5 R

FOREIGN PATENT DOCUMENTS 1,368,532  9/1974  United Kingdom.

*Primary Examiner*—Jose Tovar
*Attorney, Agent, or Firm*—James A. Costello

[57] ABSTRACT

Mannich condensation products useful in gasoline as carburetor detergents; the condensation compositions having the formula

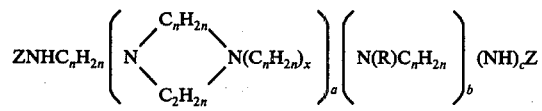

wherein Z is an alkyl - and hydroxy - substituted benzyl group wherein the alkyl has 20 to 1000 carbon atoms, $n$ is 2 or 3; R is an alkyl of 1 to 20 carbon atoms; $a$, $x$ and $c$ are each 0 or 1; and $b$ is 0 to 5; with the provisos that when $a = 0$, then $b$ is at least 1 and $c = 1$; when $a = 1$ and $x = 0$, then $b$ and $c = 0$; and when $a = 1$ and $x = 1$, then $c = 1$.

9 Claims, No Drawings

MANNICH BASES CONTAINING TERTIARY AMINES

CROSS-REFERENCE TO RELATED APPLICATION

This is a divisional application of my copending patent application, Ser. No. 612,726, filed on Sept. 12, 1975, now Pat. No. 4,054,422, issued Oct. 18, 1977.

BACKGROUND OF THE INVENTION

This invention concerns Mannich condensation products useful as additives in gasoline and lubricating oils.

The accumulation of deposits in certain critical areas of the fuel intake system in an internal combustion engine frequently causes difficulties. Thus, deposit accumulation on the carburetor throttle plate and in the area surrounding the throttle plate can cause rough idling, engine stalling and the loss of fuel economy. A very high accumulation of deposits on intake valves can lead to improper valve closing, sluggish valve action, loss of power and even valve burning. It is known that the use of a particular gasoline additive to overcome one type of difficulty very often causes other difficulties. For example, the use of a highly polar carburetor detergent to control carburetor deposits may give rise to increased intake valve deposits.

Certain condensation products of an alkylphenol, an aldehyde and an amine, commonly known as Mannich Bases, are effective carburetor detergents in gasoline. In common with most other carburetor detergents, however, these Mannich Bases can cause significantly increased intake valve deposits, particularly when used in low concentrations.

The present invention concerns a novel class of Mannich Bases which provide carburetor detergency. In contrast to the Mannich Bases of the art, the present compositions at low concentrations have a minimal effect upon the intake valve deposit weight increase and at high concentrations provide control or even reduction of the deposit weights.

SUMMARY OF THE INVENTION

This invention concerns compositions of the formula

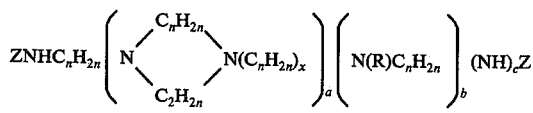

wherein Z is an alkyl- and hydroxy-substituted benzyl group wherein the alkyl has 20 to 1000 carbon atoms; $n$ is 2 or 3; R is an alkyl of 1 to 20 carbon atoms; $a$, $x$, and $c$ are each 0 or 1; and $b$ is 0 to 5; with the provisos that when $a = 0$, then $b$ is at least 1 and $c = 1$; when $a = 1$ and $x = 0$, then $b$ and $c = 0$; when $a = 1$ and $x = 1$, then $c = 1$.

Preferred compositions are those wherein the alkyl group in Z has 50 to 200 carbon atoms and wherein:
(i) $n = 2$, $a = 1$, $x = 1$, $b = 0$ and $c = 1$,
(ii) $n = 2$, $a = 1$, $x = 0$, $b = 0$ and $c = 0$,
(iii) $n = 2$, $a = 0$, $b = 1$ to 5 and $c = 1$, and
(iv) $n = 3$, $a = 0$, $b = 1$ to 5 and $c = 1$.

Most preferred are compositions wherein the alkyl group in Z has 50 to 75 carbon atoms having the formulas:

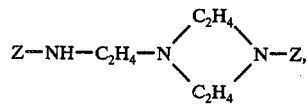

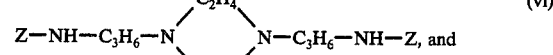

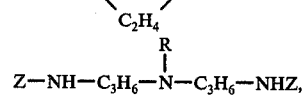

$$Z-NH-C_3H_6-\overset{R}{\underset{|}{N}}-C_3H_6-NHZ, \quad (vii)$$

wherein R is an alkyl group of 1 to 4 carbon atoms, preferably one carbon atom.

Also included within the scope of this invention are gasoline compositions containing from about 0.005 to 0.06 weight percent (12.5 to 150 pounds per thousand barrels) of the amine compositions of this invention. The amine compositions can also be used in lubricating oils to provide detergency. Normally, the lubricating oils will contain from about 0.5 weight percent to 15 weight percent of the invention composition. The invention also concerns a concentrated solution of the amine compositions in a hydrocarbon solvent boiling in the gasoline boiling range of 32° C to 205° C, said composition being present at from 10 to 90 weight percent of the solution.

DETAILS OF THE INVENTION

The amine compositions of this invention can be prepared by known methods such as alkylation of a suitable amine with an alkyl- and hydroxy-substituted benzyl halide. They are preferably prepared by the Mannich reaction wherein an alkylphenol, a suitable amine and formaldehyde are mixed and heated to a temperature in the range of about 80° to 200° C, for a time sufficient for the reaction to occur. While not required, an acidic catalyst such as hydrochloric acid or sulfuric acid can be used. The reaction mixture is kept at the reaction temperature until sufficient water of condensation has been evolved and removed.

The reaction can be carried out in the absence of a solvent but it is preferable to use one, especially one which distills with water azeotropically. Suitable solvents are hydrocarbons boiling in the gasoline boiling range of about 32° C to 205° C and include among others: hexane, cyclohexane, n-octane, isooctane, benzene, toluene, xylene and mixtures thereof. The amount of solvent used is not critical but when used it is usually employed in an amount of about 10% to 90% by weight of the total reaction mixture.

The use of a solvent not only facilitates the reaction but some or all of the solvent can be retained with the reaction product to provide the additive composition as a solution. Such a solution makes handling and incorporation of the composition into gasoline easier. The solution will preferably contain 40% to 80%, more preferably 50% to 75% by weight of the invention composition in a single solvent or a mixture of solvents such as those listed above.

The alkylphenol useful in the preparation of the invention composition is preferably a monoalkylphenol where the alkyl group has 20 to 1000 carbon atoms. Alkylphenols are well known and any of the several methods known in the art, such as the Friedel-Craft alkylation of phenol with an olefin, can be used for their preparation. Where the compositions are intended to provide control of quick-heat intake manifold deposits it is preferred, although not necessary, that the alkylphenol have an alkyl group of 50 to 1000 carbon atoms and that at least about 60% of the alkyl group be located para to the phenolic hydroxyl group. Such an alkylphenol can be prepared by the alkylation of phenol with a monoolefin of 50 to 1000 carbon atoms using boron trifluoride catalyst and a reaction temperature below about 65° C, preferably in the range 40 to 50° C.

The olefin used to alkylate the phenol is a monoolefin of 20 to 1000 carbon atoms. Preferred are monoolefins containing from 50 to 100 carbon atoms prepared from polymerization of low molecular weight olefin of 2 to 6 carbon atoms either as a homopolymer or as a copolymer. The most preferred monoolefins are homopolymers of propylene having 50 to 75 carbon atoms.

As mentioned, the alkyl-substituted phenol is preferably a monoalkylphenol but the presence of minor amounts of di- or tri-alkylphenols including those which may be found in the alkylation reactions are not objectionable.

The formaldehyde reactant can be free formaldehyde, an aqueous solution of formaldehyde or a polymerized form of formaldehyde which can provide monomeric formaldehyde under the reaction conditions.

Suitable amines are represented by the formula

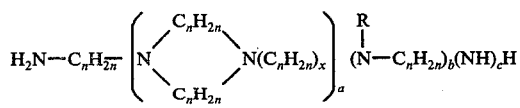

where $n$, $R$, $a$, $x$, $b$ and $c$ are as defined above with regard to their presence in the final product.

Included among the suitable amines are alkylene polyamines where $a = 0$ in the above formula and wherein there are at least three amino-nitrogens and each non-terminal aminonitrogen is a tertiary aminonitrogen, as in diethylenetriamine, triethylenetetramine, tetraethylenepentamine, hexaethyleneheptamine, dipropylenetriamine, tripropylenetetramine, tetrapropylenepentamine, pentapropylenehexamine, and hexapropyleneheptamine where each non-terminal amino-nitrogen has an alkyl substituent of 1 to 20 carbon atoms, e.g. methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonodecyl and eicosyl. The alkyl substituents can be straight chain or branched chain. Where the alkylene group in the polyalkylenepolyamine is a propylene group, it can be either a 1,2- or a 1,3-propylene group or a mixture of 1,2- and 1,3-propylene groups. Mixtures of polyamines can be used.

The preferred polyalkylenepolyamines have $n = 3$ and $x = 1$, that is, di-1,3-propylenetriamines of the formula, $H_2N\text{-}CH_2CH_2CH_2\text{-}N(R)\text{-}CH_2CH_2CH_2\text{-}NH_2$, where R is as previously defined. Many of the dipropylenetriamines are commercially available or can be readily prepared by the well-known reaction comprising condensation of a primary amine, $RNH_2$, with acrylonitrile to form, $RN(CH_2CH_2CN)_2$, which upon reduction, for example, by hydrogenation, forms a dipropylenetriamine, $RN(CH_2CH_2CH_2NH_2)_2$. The primary amine used to prepare the dipropylenetriamine can be any aliphatic primary monoamine of 1 to 20 carbon atoms. Preferred are the lower alkylamines of 1 to 4 carbon atoms, most preferably methylamine. Thus, in the preferred dipropylenetriamines R is methyl, ethyl, propyl or butyl, most preferably methyl.

Also included among suitable amines are those containing cyclic amino-nitrogen where $a = 1$ in the above formula, particularly those containing a piperazine ring where $n = 2$ in the ring structure. Representative examples of such amines are: N-aminoethylpiperazine, N,N'-bis(aminoethyl)piperazine, N-aminoethylpiperzine, N-aminopropylpiperazine and N,N'-bis(aminopropyl)piperazine. All of the suitable amines discussed above are available commercially or can be prepared readily by methods well-known in the art.

While the compositions of the present invention are more conveniently prepared by reacting an alkylphenol formaldehyde and a suitable amine by the above-described Mannich reaction, these compositions can also be prepared by other methods known to those skilled in art. For example, a compound of the formula, $Z\text{-NH-}CH_2CH_2\text{-N(H)-}CH_2CH_2\text{-NH-Z}$, where Z is as defined can be prepared by condensing an alkylphenol, formaldehyde and diethylenetriamine. The non-terminal aminonitrogen which is a secondary amino-nitrogen can be alkylated with an alkyl halide to provide the present invention composition. The above secondary amino-nitrogen can also be converted to a tertiary amino-nitrogen by the reaction of formaldehyde and formic acid whereby the substituent will be a methyl group.

As indicated by the generic formula, the amine composition of this invention is characterized by (1) the presence of at least three amino-nitrogens; (2 the presence of two alkyl- and hydroxy-substituted benzyl groups; and (3) each of the non-terminal amino-nitrogen is a tertiary amino-nitrogen. Compounds of the invention (where Z and R are as defined) include, among others

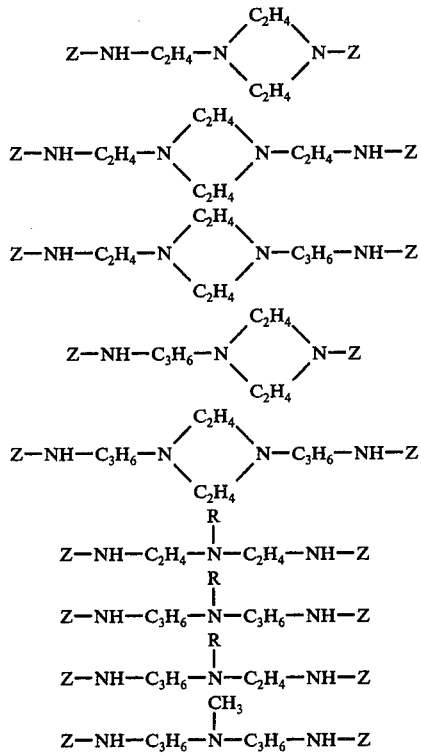

Gasolines into which the compositions of the present invention are incorporated are normally mixtures of hydrocarbons boiling in the gasoline range, usually from about 32° to 205° C. They can consist of straight chain or branched chain paraffins, cycloparaffins, olefins and aromatic compounds or any mixture of such hydrocarbons obtainable from straight run naphtha, polymer gasoline, natural gasoline, thermally or catalytically cracked hydrocarbon stocks and catalytically reformed stocks. The gasolines can also contain varying amounts of conventional additives such as antiknock compounds including tetramethyllead, tetraethyllead, mixed alkylleads, scavenging agents, dyes, antioxidants, antiicing agents, rust inhibitors, detergents, antipreignition agents as well as intake valve deposit control additives such as nonvolatile mineral lubricating oils of 500 to 1500 SUS viscosity at 38° C, and low molecular weight polypropylenes and polybutylenes.

The amount of the present composition to be incorporated into gasoline will depend upon the particular benefit desired. At about 0.005 weight percent (12.5 pounds per thousand barrels ptb), the composition will provide carburetor detergency. However, at this level some increase in the intake valve deposit weight may be obtained. At about 0.022 to 0.026 weight percent (55 to 65 ptb) there will be obtained both carburetor detergency and a neutral effect on the intake valve deposit weight, i.e. no increase in deposit weight over the base fuel. At about 0.028 weight percent (70 ptb) and higher, both carburetor detergency and a reduction in the intake valve deposit weight will be obtained. While concentrations greater than 0.06 weight percent can be used, no additional benefits are seen by such usage.

The following Examples are meant to illustrate the invention.

EXAMPLE 1

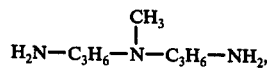

Preparation of Z—NH—C₃H₆—N(CH₃)—C₃H₆—NH—Z

A 75% by weight solution in toluene of polypropylenephenol (prepared from polypropylene M.W. 840 and phenol), 300 g, methyliminobispropylamine,

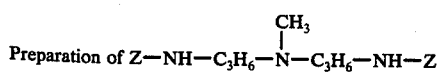

H₂N—C₃H₆—N(CH₃)—C₃H₆—NH₂, 14.5 g, and 36% by weight aqueous formaldehyde solution, 17 g, were placed in a reaction flask equipped with an agitator, a reflux condenser and a Dean-Stark water separator. The reaction mass was refluxed for 11 hours during which time 14.5 ml of water was collected and removed. Infra-red analysis of the reaction mixture indicated that the polypropylenephenol had reacted. The analytical data on the product (a sample isolated by removing toluene) were: % C, 81.5, % H, 12.0, % N, 2.0 and M.W. 1368. An additional 21.5 g of toluene was added to the reaction mixture to provide the reaction product as a 70% by weight solution in toluene.

EXAMPLE 2

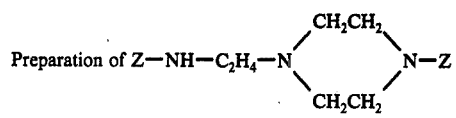

Preparation of Z—NH—C₂H₄—N(CH₂CH₂)₂N—Z

A 75% by weight solution in toluene of polypropylenephenol (prepared from polypropylene M.W. 840 and phenol), 300 g, N-aminoethylpiperazine, 12.9 g, and a 36% solution of aqueous formaldehyde, 17 g, were placed in a reaction flask equipped with an agitator, a reflux condenser and a Dean-Stark water separator. The reaction mixture was refluxed and 15.5 ml of water was collected and removed. The reaction mixture was filtered to provide 263 g of clear-brown product.

EXAMPLE 3

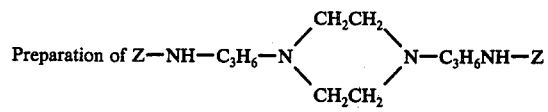

Preparation of Z—NH—C₃H₆—N(CH₂CH₂)₂N—C₃H₆NH—Z

The procedure of Example 2 was followed except that N,N'-bis(aminopropyl)piperazine, 19.2 g, was used instead of N-aminoethylpiperazine.

EXAMPLE 4 AND COMPARISONS A AND B

Carburetor Detergency

The carburetor detergency test (Onan) is carried out in a single cylinder engine to which a controlled amount of exhaust gas from another engine is mixed with the air supplied to a test carburetor. The test carburetor throat consists of a two-piece stainless steel liner fitted around the throttle plate shaft. The liner is easily removed for inspection and rating. The engine is operated under cycling conditions of one minute idling and three minutes of part throttle for an overall test period of two hours. A visual rating scale (Onan rating) of 10 for a clean carburetor and 0 for a very dirty carburetor is used. Generally, a rating of about 7 indicates satisfactory carburetor detergency.

Carburetor detergency tests were carried out with the compound of Example 1. For comparison purposes, the tests were also carried out with a compound of the formula, Z—NH—C₂H₄—N(H)—C₂H₄—NH—Z, (not of this invention, prepared by reacting two moles each of alkylphenol and formaldehyde per mole of diethylenetriamine) and a compound of the formula, Z—NH—C₂H₄—N(Z)—C₂H₄—NH—Z, (not of this invention, prepared by reacting three moles each of alkylphenol and formaldehyde per mole of diethylenetriamine) where Z represents an alkyl- and hydroxy-substituted benzyl group where the alkyl group is a polypropylene group of 840 molecular weight. It is to be noted that the comparison compounds differ essentially from the invention compound used in this test by having either a H or Z substituent on the nonterminal aminonitrogen instead of a methyl group. The results are summarized in Table 1.

Table 1

| Example or Comparison | Carburetor Detergency Tests Compound | ptb | Onan Rating |
|---|---|---|---|
| Comparison A | Z–NH–C$_2$H$_4$–N(H)–C$_2$H$_4$–NH–Z | 15 | 7.8 |
| Comparison B | Z–NH–C$_2$H$_4$–N(Z)–C$_2$H$_4$–NH–Z | 15 | 5.1 |
| Example 4 | Z–NH–C$_3$H$_6$–N(CH$_3$)–C$_3$H$_6$–NH–Z | 14 | 7.6 |

The compound of Comparative Example A which has a secondary amino-nitrogen as the nonterminal amino-nitrogen has good carburetor detergency. In Comparative Example B where the compound has a tertiary amino-nitrogen as the nonterminal amino-nitrogen, carburetor detergency is lost. Thus, the compound of this invention, which has a tertiary aminonitrogen as the nonterminal amino-nitrogen, would also be expected not to have good detergency. On the contrary, however, the results show that the compound of this invention at 14 ptb is an effective carburetor detergent (Onan Rating of 7.6).

EXAMPLES 5 to 7 AND COMPARISONS C AND D

Intake Valve Deposit Tests

Intake valve deposit tests were carried out in a 1974 Buick with 455 CID engine equipped with an exhaust gas recirculation (EGR) system. Completely reconditioned heads with weighed intake valves were installed before the tests. Deposits from piston heads were removed and the intake manifold was solvent-cleaned. New spark plugs, points, PCV valve, air filter and oil filter were installed. Carburetor adjustments and timing were carried out according to the manufacturer's specifications.

Mileage accumulation (6000 miles) was carried out on a Programmed Chassis Dynamometer according to AMA City Driving Schedule (Federal Register Vol. 33 No. 2, Jan. 4, 1968). Fuels used were industry-known Indolene and Indolene containing 2 g/gal. of tetraethyllead antiknock compound.

At the conclusion of the test, the intake valves were removed and weighed. The deposit weight was expressed as an average weight per valve. The intake valve tulip deposits were also rated using the standard CRC merit rating scale wherein a clean valve tulip has a rating of 10. Deposits on the valve stems were also rated with a clean stem having a rating of 10. The stem rating is carried out by comparison with a standard photographic scale. The results are summarized in Table 2.

Table 2

| Example or Comparison | Additive (ptb) | Fuel | Intake Valve Deposit (g/valve) | Tulip Rating | Stem Rating |
|---|---|---|---|---|---|
| Comparison C | None | Indolene | 2.10 | 6.2 | 5.2 |
| Example 5 | of Example 1 (70 ptb) | Indolene | 1.99 | 5.4 | 8.4 |
| Comparison D | None | Indolene + 2 g Pb | 3.04 | 6.1 | 5.3 |
| Example 6 | of Example 1 (14 ptb) | Indolene + 2 g Pb | 4.55 | 5.6 | 3.5 |
| Example 7 | of Example 1 (70 ptb) | Indolene + 2 g Pb | 2.68 | 5.7 | 8.9 |

The above results show that the invention composition at 70 pounds per thousand barrels provides reduction in the intake valve deposit weights over those of the Comparison (control) fuels. At 14 ptb, there is an increase of about 50% in the deposit weight. Particularly notable and promising are the valve stem ratings with the invention composition at 70 ptb, Examples 5 and 7. The outstanding improvements in the stem ratings also attest to the beneficial effects of the present composition since valve stem ratings are often considered to be indicative of potential valve sticking.

EXAMPLES 8 to 11

Induction System Deposits

The induction system deposit (ISD) tests were carried out by the modified bench test of Johnston and Dimitroff, SAE Transactions Vol. 75 (1967) Paper No. 660,783. The test consists of spraying gasoline and air onto a heated preweighed metal tube. At the conclusion of the test, the metal tube is removed from the apparatus, washed with heptane and weighed. The weight of the deposit to the nearest 0.1 mg indicates the deposit-forming tendency of the fuel. The following test conditions were used:

Fuel: 100 ml Indolene containing 10 volume percent of 10%
Indolene distillation bottoms and 0.05 volume percent of used crankcase oil ("Uniflo," 3300 miles)
Fuel Flow: 2 cc/min
Air Flow: 0.5 cu ft/min
Billet Temperature: 288° C.

The effects of the composition of Example 1 on the induction system deposits were determined by adding the composition (as 70% solution in toluene) in the indicated amounts to the above-described fuel and determining the amount of the deposit formed. The results are expressed in terms of percent deposit weight change compared to the deposit weight obtained with the base fuel. The results are summarized in Table 3.

Table 3

| Example | Induction System Deposit (ISD) Tests Additive (ptb) | ISD % Deposit Weight Change |
|---|---|---|
| Example 8 | of Example 1 14 ptb | +49 |
| Example 9 | of Example 1 35 ptb | +29 |
| Example 10 | of Example 1 70 ptb | −22 |
| Example 11 | of Example 1 105 ptb | −39 |

The ISD test results show that the present invention composition provides slightly increased induction system deposits at the lower concentrations but that the deposit weights are decreased at higher concentrations. The results show good correlation with the intake valve deposit tests. By interpolation of the above data, it can be seen that the present compositions at 55 to 65 pounds per thousand barrels cause no increase in induction system deposits (and also presumably no increase in the intake valve deposits) and that at higher concentrations they provide for the reduction in the deposit weights.

EXAMPLE 12 AND COMPARISON E

Octane Requirement Increase

The effect of the invention compositions on the octane requirement increse (ORI) of an engine was determined on a clean Ford 302 CID V8 engine on a test stand. The fuel was unleaded Indolene. The engine was operated on a modified AMA driving schedule (Federal Register Vol. 33 No. 2, January 4, 1968) which simulated an urban and suburban driving cycle averaging about 30 miles per hour. The octane requirements were determined using primary reference fuels, the test being continued until equilibrium octane requirement of the engine was established.

The composition of Example 1 was added to the fuel as a 70% by weight solution in toluene at 100 pounds per thousand barrels (ptb) thereby providing the composition at 70 ptb. Additionally, at the end of the test, the intake valves were inspected for deposits and cleanliness. The results, summarized in Table 4, show that the composition of the invention does not add to the octane requirement increase of the fuel and reduces the intake valve deposit weight and keeps the valves clean at the concentration employed.

Table 4

| Example or Comparison | Additive (ptb) | to Stable ORI | Total Operation | ORI | Intake Valves Wt. g/valve | Tulip Rating | Stem Rating |
|---|---|---|---|---|---|---|---|
| Comparison E | None | 500 | 633 | 9.4 | 3.3 | 5.3 | 3.8 |
| Example 12 | of Example 1 (70 ptb) | 375 | 592 | 8.0 | 0.3 | 7.7 | 7.5 |

The embodiments of the invention in which an exclusive property or privilege is claimed are defined as follows:

1. A composition of the formula

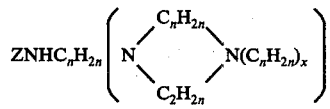

wherein Z is an alkyl- and hydroxy-substituted benzyl group wherein the alkyl has 20 to 1000 carbon atoms; $n$ is 2; $x$ and $c$ are each 0 or 1; with the provisos that when $x = 0$, then $c = 0$; and when $x = 1$, then $c = 1$.

2. A composition according to claim 1 wherein the alkyl group in Z has 50 to 200 carbon atoms.

3. A composition according to claim 2 wherein $x = 1$, and $c = 1$.

4. A composition according to claim 2 wherein $x = 0$, and $c = 0$.

5. A composition according to claim 2 wherein the alkyl group in Z has 50 to 75 carbon atoms.

6. A composition according to claim 5:

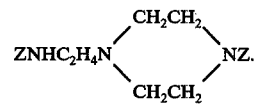

7. A gasoline composition containing from 0.006 to 0.06 weight percent of the composition according to claim 1.

8. A concentrated solution in a hydrocarbon solvent boiling in the gasoline boiling range of 32° C to 205° C, of from 10 to 90 weight percent of the composition according to claim 1.

9. A composition according to claim 5,

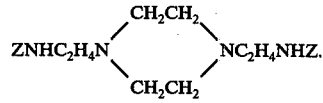

* * * * *

UNITED STATES PATENT OFFICE
CERTIFICATE OF CORRECTION

PATENT NO. : 4,121,911
DATED : October 24, 1978
INVENTOR(S) : Bruce Hollis Garth It is certified that error appears in the above—identified patent and that said Letters Patent are hereby corrected as shown below:

In the Abstract, the formula should read as follows:

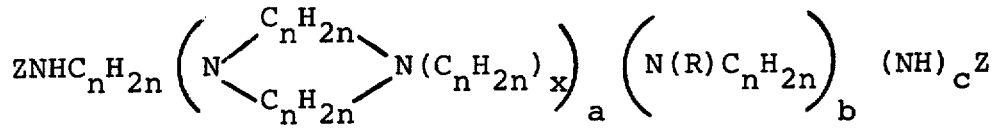

In the Summary of the Invention, at column 1, line 50, the formula should read as follows:

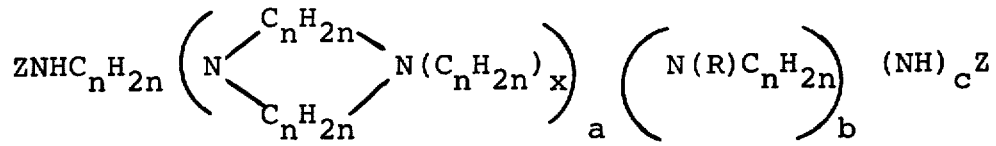

In Claim 1, column 10, at line 15, the formula should read as follows:

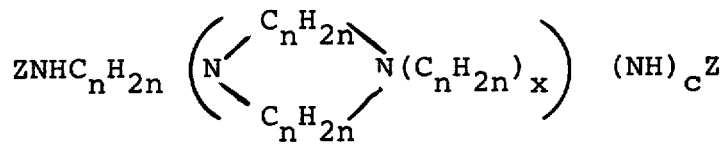

Signed and Sealed this

Nineteenth Day of June 1979

[SEAL]

Attest:

RUTH C. MASON
Attesting Officer

DONALD W. BANNER
Commissioner of Patents and Trademarks